(12) United States Patent
Wagner (10) Patent No.: US 7,678,538 B2
(45) Date of Patent: Mar. 16, 2010

(54) DISINFECTION OF BIOLOGICAL FLUIDS USING ASYMMETRIC CYANINE DYES

(75) Inventor: Stephen J. Wagner, Columbia, MD (US)

(73) Assignee: American National Red Cross, Wsahington, DC (US)

( * ) Notice: Subject to any disclaimer, the term of this patent is extended or adjusted under 35 U.S.C. 154(b) by 528 days.

(21) Appl. No.: 11/430,848

(22) Filed: May 10, 2006

(65) Prior Publication Data

US 2006/0257844 A1      Nov. 16, 2006

Related U.S. Application Data

(60) Provisional application No. 60/680,502, filed on May 13, 2005.

(51) Int. Cl.
*A01N 1/02* (2006.01)
*C12N 7/04* (2006.01)

(52) U.S. Cl. ............................. 435/2; 546/236; 546/238; 546/325

(58) Field of Classification Search ..................... 435/2, 435/236, 238, 325
See application file for complete search history.

(56) References Cited

U.S. PATENT DOCUMENTS 4,915,683 A * 4/1990 Sieber ........................ 604/5.02
5,798,238 A * 8/1998 Goodrich et al. ......... 435/173.3
6,022,961 A    2/2000 Yamamoto et al.
6,242,477 B1   6/2001 Okamoto et al.

OTHER PUBLICATIONS

Davila et al. "Inactivation of tumors and viruses via efficient photoisomerism" J. Chem. Soc., Chem. Comm. (1989) 17:1215-1216.*
Prodhomme et al. "A theoretical and experimental study of two thiazole orange derivatives with single- and double-stranded oligonucleotides, polydeoxyribonucleotides and DNA" J. Photochem. Photobiol, B: Biology (1993) 53: 60-69.*
Boger et al. "Thiazole orange as the fluorescent intercalator in a high resolution assay for determining DNA binding affinity and sequence selectivity of small molecules" Bioorg. Med. Chem. (2001) 9: 2511-2518.*
Petty et al. "Thermodynamic characterization of the association of cyanine dyes with DNA" J. Phys. Chem. B (2000) 104: 7221-7227.*
Abe et al. "Analysis of Viral DNA, Protein and Envelope Damage After Methylene Blue, Phthalocyanine Derivative or Merocyanine 540 Photosensitization" *Photochem Photobiol* (1995) 61(4):402-9, American Society for Photobiology.
Abe et al. "Factors Affecting M13 Bacteriophage Inactivation by Methylene Blue Photosensitization" *Photochem Photobiol* (1997) 65(5):873-876.
Besselink et al. "The Band III Ligand Dipyridamole Protects Human RBCs During Photodynamic Treatment while Extracellular Virus Inactivation is Not Affected" *Transfusion* (Jun. 2002) 42:728-33.

Besselink et al. "Composition of the Additive Solution Affects Red Blood Cell Integrity After Photodynamic Treatment" *Vox Sang* (Jul. 2003) 85:183-9, Blackwell Publishing.
Beutler A Manual of Biochemical Methods. Third Edition, by Earnest Beutler. Grune & Stratton Inc. Orlando, FL (1984) pp. 122-123.
Dodd et al., "Current Prevalence and Incidence of Infectious Disease Markers and Estimated Window-Period Risk in the American Red Cross Blood Donor Population" *Transfusion* (Aug. 2002) 42:975-9.
Fiebig et al. "Emerging Infections in Transfusion Medicine" *Clin. Lab Med* (Sep. 2004) 24:797-823, Elsevier, Inc.
Hanson "Photochemical Inactivation of Viruses with Psoralens: An Overview" *Blood Cells* (1992) 18:7-25, Springer-Verlag, New York.
Horowitz et al. "Inactivation of Viruses in Red Cell and Platelet Concentrates with Aluminum Phthalocyanine (AlPc) Sulfonates" *Blood Cells* (1992) 18:141-50, Springer-Verlag, New York.
Lavie et al., "Hypericin as an Inactivator of Infectious Viruses in Blood Components" *Transfusion* (1995) 35(5):392-400.
Macedo de Oliveira et al., "West Nile Virus Blood Transfusion-related Infection Despite Nucleic Acid Testing" *Transfusion* (Dec., 2004) 44:1695-9.
North et al. "Viral Inactivation in Blood and Red Cell Concentrates with Benzoporphyrin Derivative" *Blood Cells* (1992) 18:129-40, Springer-Verlag, New York.
Pealer et al. "Transmission of West Nile Virus Through Blood Transfusion in the United States in 2002" *N Engl J Med* (Sep. 25, 2003) 349:1236-45, Massachusetts Medical Society.
Pooler "The Kinetics of Colloid Osmotic Hemolysis. II. Photohemolysis" *Biochim Biophys Acta* (1985) 812:199-205, Elsevier Science Publishers, B.V.
Rywkin et al. "Importance of Type I and Type II Mechanisms in the Photodynamic Inactivation of Viruses in Blood with Aluminum Phthalocyanine Derivatives" *Photochem Photobiol* (1992) 56(4):463-9, Pergamon Press Ltd, Great Britain.
Shepherd et al. "West Nile Virus Encephalitis in a Kidney Transplant Recipient" *Am J. Transplant* (May 2004) 4:830-3, Blackwell Munksgaard.
Skripchenko et al. "Comparison of Methylene Blue and Methylene Violet for Photoinactivation of Intracellular and Extracellular Virus in Red Cell Suspension" *Photochem Photobiol* (1997) 65(3):451-455, American Society for Photobiology.
Standefer et al. "Use of Tetramethylbenzidine in Plasma Hemoglobin Assay" *Clin Chem* (1977) 23(4):749-51.
Wagner et al., "Red Cell Alterations Associated With Virucidal Methylene Blue Phototreatment" *Transfusion* (1993) 33:30-6.

(Continued)

*Primary Examiner*—Sandra Saucier
*Assistant Examiner*—Susan Hanley
(74) *Attorney, Agent, or Firm*—Buchanan Ingersoll & Rooney PC (57) ABSTRACT

Asymmetric cyanine dyes of Formula I bind nucleic acid but not red blood cell membrane, and function as photosensitizers when rigidly bound but not when free in solution. Unbound dye thus causes minimal oxidative damage. The dyes do not substantially accumulate in red blood cells, thereby minimizing hemolysis due to oxidative damage. Biological fluids can be disinfected by mixing the fluid with these asymmetric cyanine dye that binds to nucleic acid, irradiating the mixture, and recovering clinically significant components from the biological fluid and/or assaying the fluid for pathogens.

24 Claims, 5 Drawing Sheets

OTHER PUBLICATIONS

Wagner et al. "Differential Sensitivities of Viruses in Red Cell Suspensions to Methylene Blue Photosensitization" *Transfusion* (1994) 34:521-526.

Wagner et al. "Factors Affecting Virus Photoinactivation by a Series of Phenothiazine Dyes" *Photochem Photobiol* (1998) 67(3):343-349, American Society for Photobiology.

Wagner et al. "Preservation of Red Cell Properties After Virucidal Phototreatment with Dimethylene Blue" *Transfusion* (1998) 38:729-737.

Wagner et al. "Use of a Flow-Cell System to Investigate Virucidal Dimethylmethylene Blue Phototreatment in Two RBC Additive Solutions"*Transfusion* (Sep. 2002) 42:1200-1205.

Wagner et al. "Quinacrine Enhances Vesicular Stomatitis Virus Inactivation and Diminishes Hemolysis of Dimethylmethylene Blue-phototreated Red Cells" *Photochem Photobiol* (Aug. 28, 2002) 76(5):514-517.

Wagner et al. "Use of a Flexible Thiopyrylium Photosensitizer and Competitive Inhibitor for Pathogen Reduction of Viruses and Bacteria With Retention of Red Cell Storage Properties" *Transfusion* (May 2005) 45:752-60.

Yamada et al., "Inhibition of Growth of HIV by Human Natural Interferon in vitro," *AIDS Res Human Retroviruses*, (1988) 4(4):287-94, Mary Ann Liebert, Inc. Publishers.

Yamamoto et al., "Novel Intercalators of Pyrylium Dye into Double-Stranded DNA" *Nucleic Acids Symp* 29:83-84 (1993), Oxford University Press.

Zou et al., "Patterns of Age- and Sex-Specific Prevalence of Major Blood-Borne Infections in United States Blood Donors, 1995 to 2002: American Red Cross Blood Donor Study" *Transfusion* (Nov. 2004) 44:1640-9.

Jill M. O'Brien et al., "Evaluation of Merocyanine 540-Sensitized Photoirradiation as a Means to Inactivate Enveloped Viruses in Blood Products," JLab Clin Med (1990) 116: 439-447.

Sieber et al., "Antiviral Effects of Photosensitizing Merocyanine Dyes: Implications for Transfusion and bone Marrow Transplanation," Sem Hematol (1992) 29: 79-87.

Tymish Y. Ohulchanskyy et al., ""Switched-On" Flexible Chalcogenopyrylium Photosensitizers. Changes in Photophysical Properties Upon binding to DNA", *J. Phys. Chem.* B (2007) 111: 9686-9692, American Chemical Society.

Andrey Skripchenko et al, "Thiazole Orange, a DNA-binding Photosensitizer with Flexible Structure, Can Inactivate Pathogens in Red Blood Cell Suspensions While Maintaining Red Cell Storage Properties", *Transfusion*, 46:213-219 (2006).

Bjorn Akerman and Eimer Tuite, "Single-and Double-Strand Photocleavage of DNA by YO, YOYO, and TOTO", *Nucleic Acids Research* (1996) 24:6, pp. 1080-1090, Oxford University Press.

\* cited by examiner

FIGURE 1

Thiazole Orange
$R^1 = CH_3$
$R^2 = CH$
$R^3 = CH_3$

DISINFECTION OF BIOLOGICAL FLUIDS USING ASYMMETRIC CYANINE DYES

This application claims benefit under 35 USC 119(e) of provisional application Ser. No. 60/680,502, filed May 13, 2005.

STATEMENT REGARDING FEDERALLY SPONSORED RESEARCH OR DEVELOPMENT

This invention was made with United States government support awarded by the National Heart Lung and Blood Institute under the following number: NHLBI No. HL66779. The United States has certain rights in this invention.

FIELD OF THE INVENTION

The invention relates to compositions and methods for disinfecting biological fluids, such as blood and blood products, by contacting the biological fluid with one or more of a class of asymmetric cyanine dyes followed by irradiation.

BACKGROUND OF THE INVENTION

Transmission of many infectious agents by transfusion has dramatically declined due to improved testing methods and careful donor selection (Dodd R Y et al. *Transfusion* 2002; 42:975-9; Zou S et al. *Transfusion* 2004; 44:1640-9; Fiebig E W et al. *Clin Lab Med* 2004; 24:797-823). However, other pathogens for which there are no licensed tests or those emerging pathogens for which we have limited knowledge may pose blood borne infectious risks. The recent outbreak of West Nile virus infection in blood and organ recipients demonstrated the vulnerability of the blood supply to emerging and re-emerging pathogens (Macedo de Oliveira A et al. *Transfusion* 2004; 44:1695-9; Shepherd J C et al. *Am J Transplant* 2004; 4:830-3; Pealer L N et al. *N Engl J Med* 2003; 349: 1236-45). Although the period of high risk to recipients was brief due to the rapid implementation of NAT testing, other agents may not be as amenable to successful test development. Therefore, there is a continued need to investigate broad spectrum inactivation methods for blood components.

One approach to pathogen reduction is treatment using photosensitizing dyes (Horowitz B et al. *Blood Cells* 1992; 18:141-50' Lavie G et al. *Transfusion* 1995; 35:392-400; North J et al. *Blood Cells* 1992; 18:129-40; Rywkin S et al. *Photochem Photobiol* 1992; 56:463-9; Wagner S J et al. *Transfusion* 1992; 33:30-6; Abe H et al. *Photochem Photobiol* 1995; 61, 402-9; Skripchenko A et al. *Photochem Photobiol* 1997; 65:451-455; Abe H et al. *Photochem Photobiol* 1997; 65:873-876; Wagner S J et al. *Photochem Photobiol* 67:343-349, 1998; Wagner S J et al. *Transfusion* 38:729-737, 1998; Besselink G A et al. *Transfusion* 2002 June; 42:728-33; Wagner S et al. *Transfusion* 2002; 42:1200-1205; Wagner S J et al. *Photochem Photobiol* 2002; 76:514-517). Although some investigators have studied photosensitizers which bind to viral membranes or capsids for pathogen reduction in red blood cells (RBCs), we have focused our efforts on utilizing nucleic acid binding dyes because this approach, in theory, specifically targets pathogens while leaving anucleate RBCs intact. Unfortunately, RBCs phototreated with these dyes suffer damage from reactive oxygen species generated by photosensitizer bound to the erythrocyte membrane as well as photosensitizer free in solution (Besselink G A et al. *Transfusion* 2002 June; 42:728-33; Wagner S et al. *Transfusion* 2002; 42:1200-1205; Wagner S J et al. *Photochem Photobiol* 2002; 76:514-517). Therefore, nucleic acid binding does not necessarily imply that a candidate dye has no affinity to RBC proteins, glycoproteins or lipids, or that an inconsequential level of dye remains free in solution.

In a previous study, we found that the nucleic acid intercalating dye, dimethylmethylene blue, also bound to RBC membranes. Levels of RBC-bound dye could be diminished by the addition of a competitive membrane binding inhibitor, such as quinacrine, whose structure is similar to that of the sensitizer. Using quinacrine, photo-induced hemolysis from dimethylmethylene blue could be significantly reduced under conditions that maintained >6 $\log_{10}$ reduction of model viruses (Wagner S J et al. *Photochem Photobiol* 2002; 76:514-517). However, hemolysis from phototreated cells protected by the competitive inhibitor remained, possibly from photodynamic action of free dye in solution.

In order to minimize red cell damage from reactive oxygen species emanating from free dye, we investigated the use of a novel nucleic acid intercalating photosensitizer whose flexible structure is only active when dye is rigidly bound to substrate. One such flexible dye is thiopyrylium (TP), which cannot generate reactive oxygen species when free in solution because the energy from absorbed light can be dissipated through bond rotation (Wagner S J et al. *Transfusion* 2005; 45:752-60). When flexible dyes like TP are rigidly bound to substrate such as nucleic acid, the lifetime of their excited singlet state is prolonged to the nanosecond timescale; this allows for greater efficiency of fluorescence and increases the probability for intersystem crossing to the triplet state necessary for singlet oxygen mediated photochemical reactions (Wagner S J et al. *Transfusion* In press; Yamamoto N et al. *Nucleic Acids Symp Ser.* 1993; 29:83-4; Yamamoto N et al.; U.S. Pat. No. 6,022,961, 2000; Okamoto T et al. U.S. Pat. No. 6,242,477 B1, 2001). TP is a potent photosensitizer against a broad spectrum of viruses and bacteria. Unfortunately, TP also exhibits strong affinity to RBC membranes. Although photoinduced hemolysis from membrane bound TP could almost be reduced to background control levels by adding a competitive membrane binding inhibitor, dipyridamole, this approach still required the addition of two drugs to RBCs (Wagner S J et al. *Transfusion* 2005; 45:752-60).

There remains a need in the art for methods and materials capable of initiating singlet oxygen mediated photochemical reactions but which have binding specificity for pathogenic components to the exclusion of RBCs and/or other clinically significant components.

SUMMARY OF THE INVENTION

Asymmetric cyanine dyes, particularly thiazole orange, bind nucleic acids of pathogens but do not substantially accumulate in or on RBCs. Asymmetric cyanine dyes that bind nucleic acids can be used to photoinactivate a wide variety of model viruses and pathogens in biological fluids, particularly those containing RBCs, while causing limited hemolysis; and they do so without the addition of quenchers or competitive inhibitors.

The present invention provides disinfectant formulations comprising asymmetric cyanine dyes that bind nucleic acids but not cell membrane. Additionally, the invention provides methods for disinfecting biological fluids, particularly those containing RBCs. The method comprises contacting or admixing a biological fluid with an asymmetric cyanine dye, irradiating the resulting mixture, and, optionally, removing the cyanine dye and/or recovering a biologically significant component from the disinfected biological fluid.

DETAILED DESCRIPTION OF THE INVENTION

We have found that certain asymmetric cyanine dyes are effective photosensitizers in reducing a wide variety of pathogens in biological fluid. Our investigation of the phenomenon shows that certain dyes bind nucleic acid of various pathogens but do not bind cell membranes nor accumulate in RBCs in significant numbers. The dyes have the added advantage of passing through cell membranes, such as those of RBCs, without killing or destroying the cell. Moreover, the dyes pass through cell membranes without the use of permeants, such as fixatives, or similar expedients such as electroporation. These dyes are also referred to herein as nucleic acid binding, cell membrane-permeable asymmetric cyanine dyes.

When unbound, as when they are free in solution, those dyes dissipate energy without producing reactive oxygen.

An advantage of these asymmetric cyanine dyes is that they can be formulated as single-active-agent compositions and used in methods for disinfecting biological fluids. As such, they avoid the need for added agents, such as quenchers or competitive membrane binding inhibitors, which agents can increase toxicity and/or side reactions within the fluid.

In one embodiment, the nucleic acid binding, cell membrane-permeable asymmetric cyanine dye is as shown in Formula I, below:

Formula I where: $R^1$, $R^2$, and $R^3$ are saturated or unsaturated hydrocarbons of $C_6$ or fewer; $R^4$ and $R^5$ are the same or different and are selected from saturated or unsaturated hydrocarbons, acyl, aryl, alcohol, ester, aldehyde, ketone and amine of $C_4$ or fewer, any of which may be further substituted with a halogen, or $R^4$ and/or $R^5$ is itself a halogen; n is 0-5; m is 0-4; p is 0-4; and W is a fused, bicyclic heteroaryl moiety. Other embodiments are those wherein $R^1$ and $R^3$ are saturated or unsaturated hydrocarbons of $C_3$ or fewer; n, m, and p are 0, and W is a fused bicyclic heteroaryl moiety.

Figure 1:
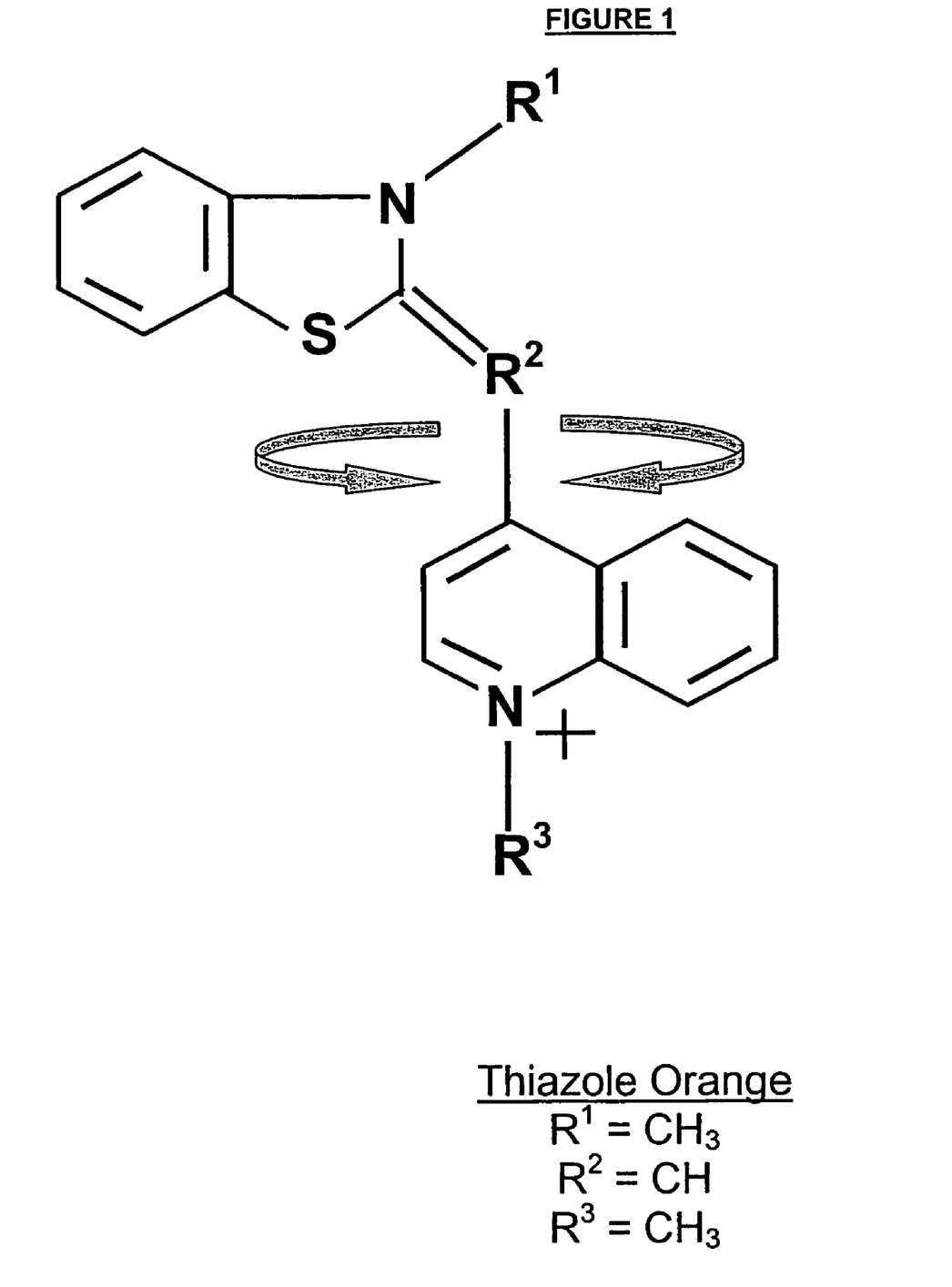
FIG. 1. Structure of thiazole orange (TO). Arrows denote bonds capable of rotation.

In still other embodiments, the nucleic acid binding, cell membrane-permeable asymmetric cyanine dyes of the invention are thiazole orange (TO; FIG. 1) and derivatives thereof. Derivatives include those wherein $R^1$, $R^2$, and $R^3$ are modified to any saturated or unsaturated hydrocarbon of $C_6$ or fewer. Thus, for example, $R^1$ and $R^3$ might be any alkyl group of $C_6$ or fewer, and $R^2$ might be any alkenyl radical of $C_6$ or fewer. Other derivatives are those wherein $R^1$, $R^2$, and $R^3$ are modified to any saturated or unsaturated hydrocarbon of $C_3$ or fewer.

Derivatives of TO also include those wherein TO is alternatively or further modified to substitute any of the heteroatoms of TO with N, O, S, or Se.

Still more derivatives are those wherein heterocyclic moieties are incorporated or substituted for the quinoline moiety and/or the benzothiazole moiety of TO. For present purposes, such heterocyclic moieties include: heteroaryl radicals of about $C_{14}$ or fewer; have one or two heteroatoms; and which can be further substituted with saturated or unsaturated hydrocarbons of about $C_6$ or fewer. In one series of embodiments, the quinoline moiety and/or the benzothiazole moiety is substituted with a fused, bicyclic heteroaryl moiety. Among those embodiments are those wherein the heteroaryl moiety has one heteroatom and those wherein the heteroaryl moiety has two heteroatoms. The substitute heteroaryl moieties can be further substituted as described above.

Additional or alternative dyes for purposes of this invention is oxazole yellow (OY) and derivatives thereof.

The nucleic acid binding, RBC membrane-permeable asymmetric cyanine dyes can be used as described herein in either monomeric or dimeric form. Additionally, these cyanine dyes can be synthesized, derivatized, or otherwise manipulated to bind particular nucleic acid sequences, thereby affording greater sensitivity and specificity for the desired pathogenic-reducing effect.

Without wishing to be bound by any theory, the present invention will be better understood by reference to the following description. Singlet oxygen can be generated from molecular oxygen by various photosensitizers following irradiation. Singlet oxygen disrupts labile bonds in biologically significant molecules, e.g., various nucleic acids and amino acids. The effect, although short-lived and highly localized, can be exploited to kill, inactivate, or destroy various biological and molecular species, such as viruses and other pathogens.

The present class of asymmetric cyanine dyes are photosensitizers that can be switched on and off. These dyes bind nucleic acid by intercalation. When irradiated in the bound state, the energy absorbed causes the dye molecule to go from a ground state to an excited singlet state, and ultimately to an excited triplet state. The triplet state molecule reacts with ground-state oxygen to create singlet oxygen, which, in turn, disrupts labile bonds in certain biologically significant molecules. Thus, asymmetric cyanine dyes are singlet oxygen generators that are active, or "switched on" only when bound.

When unbound, the dye has a higher degree of freedom, and absorbed energy is given off through rotation and/or vibration, causing little more than localized heating. Thus, when unbound dye is irradiated, it is inactive as a photosensitizer and "switched off" as a singlet oxygen generator; and the integrity of labile bonds in biological or molecular species in close proximity to the unbound dye are substantially undisturbed.

We have discovered that asymmetric cyanine dyes, especially thiazole orange, are not only singlet oxygen generators that can be switched on and off, but demonstrate a binding specificity that make them particularly useful as disinfecting agents for biological fluids, especially those containing RBCs. Asymmetric cyanine dyes, and especially thiazole orange, preferentially bind nucleic acids of a wide variety of pathogens, but do not substantially bind or accumulate in or on RBCs. Thus, a composition can be formulated that contains one or more of these asymmetric cyanine dyes as the only active ingredient, and that is suitable for disinfecting biological fluids. The composition has the added advantage of avoiding substantial hemolysis of RBCs.

The asymmetric cyanine dyes of the invention are those wherein the dye binds nucleic acid, typically by intercalation, but does not bind cellular membranes. These dyes pass through the RBC membrane without killing or substantially disrupting the structural or functional integrity of the cell. Thus, for example, these dyes can permeate enveloped viruses and, once inside, bind the nucleic acid. When irradiated with appropriate energy, the bound dye produces singlet oxygen, which destroys labile bonds within the viral DNA (or RNA), fatally disrupting its genetic machinery. Thus, pathogens containing DNA (or RNA) can be effectively and selectively destroyed, while anucleate RBCs (which are devoid of DNA) are undisturbed.

One of ordinary skill in the art will understand that additional active agents can be added to such a composition in accordance with the particular conditions and objectives. The compositions can also be formulated with additional additives and excipients including various diluents, buffers, stabilizers, preservatives, and the like.

The invention provides compositions comprising asymmetric cyanine dyes. An exemplary asymmetric cyanine dye is thiazole orange and various derivatives. The compositions are storage stable and can be used for, among other things, disinfecting biological fluids and other materials of biological or non-biological origin. The present invention further affords methods for disinfecting materials, including biological fluids and the like, without concomitant destruction of RBCs.

A particular advantage of the compounds and compositions of the present invention is that these compounds can be formulated into compositions comprising a single active agent. The compositions retain pathogen inactivating potential, and can be used in the presence of biological materials and clinically significant constituents. The compositions of the present invention can be conveniently manufactured and analyzed for, e.g., concentration, anti-pathogenic potency, efficacy, and storage stability. Thus, the compositions can be effectively standardized, and reliably compounded, packaged, and stored for subsequent use. By resort to a single-agent composition it is also more likely that the use of these compounds will result in fewer deleterious reactions or by-products.

It is contemplated that the compounds of the present invention will be useful not only in disinfecting biological fluids and other biological material in vitro, but also as an in vivo or ex vivo therapeutic for treating or preventing infection in animals, including humans.

The present invention provides a method for disinfecting a biological fluid with an asymmetric cyanine dye. The method involves combining the biological fluid and the dye, and irradiating the resulting mixture. The invention includes a method for disinfecting a biological fluid comprising: a) contacting the biological fluid with an asymmetric cyanine dye that binds nucleic acid but not cell membrane; and b) irradiating the resulting mixture.

The invention also provides a method for disinfecting a RBC-containing biological fluid that avoids destruction or loss of function of a substantial quantity of RBCs. Stated another way, the method provides high levels of pathogen reduction while minimizing or eliminating hemolysis.

In one embodiment, the method involves disinfecting a RBC-containing biological fluid by creating a mixture by combining the biological fluid with a composition comprising an asymmetric cyanine dye, incubating the resulting mixture for a period of about 5 to about 60 minutes, and irradiating the mixture.

The asymmetric cyanine dye can be added to the mixture to a quantity of about 50 to about 200 μM. Some embodiments involve the addition of about 60 to about 100 μM. In still other embodiments, the asymmetric cyanine dye is added to about 80 μM.

Irradiation can be effected with any energy source sufficient to cause the asymmetric cyanine dye to form singlet oxygen. In one embodiment, the biological fluid-dye mixture is irradiated with white light (e.g., about 1-10 $J/cm^2$ of light; and in some embodiments, about 6-9 $J/cm^2$ white light). Alternatively irradiation can be effected with light corresponding to substantial absorption by the asymmetric cyanine dye as measured spectroscopically. Thus, irradiation can be effected with light of a wavelength within the range corresponding to an absorption peak of the asymmetric cyanine dye. In the case of thiazole orange, irradiation with light of wavelength(s) within the range of about 400 to about 550 nm can be used. As such, blue light (424-491 nm) and/or green light (491-575 nm) can be used. Likewise, light of more narrow wavelength ranges within the absorption peak of the asymmetric cyanine dye can be used.

In some embodiments, the method includes the further step wherein the biological fluid is oxygenated prior to irradiation.

The method includes a further optional step of recovering pathogen-reduced (or pathogen-free) biological fluid containing RBCs wherein hemolysis in the fluid on storage at 42 days is less than about 2%. In some embodiments, the method achieves hemolysis on storage at 42 days less than about 1%; and in still others, hemolysis on storage at 42 days is less than about 0.5%.

Likewise, the method provides recovery of pathogen-reduced (or pathogen-free) biological fluid containing RBCs wherein potassium efflux from RBCs is less than 30 mM on storage at four days.

The method includes the optional step of incubating the biological fluid-cyanine dye mixture for about 5 to about 60 minutes. The incubation can be performed at under refrigeration (e.g., at about 1-6° C.), or at standard room temperature and pressure (RTP).

The method also includes the optional step of assaying the irradiated mixture for virus, bacteria, or bacteriophage. The term "assay" is used in its conventional sense, and includes a measurement of the quantity of viable and/or pathogenic virus, bacteria, and/or bacteriophage within a sample. The measurement might also be stated in terms of the $Log_{10}$ reduction of virus, bacteria, and/or bacteriophage within the sample.

As used herein, and unless stated otherwise, the term "pathogen" includes viruses, bacteria, fungi, parasites, and other micro-organisms capable of exerting pathogenic effects in multi-cellular organisms. Thus, the use of the term "pathogen" contemplates micro-organisms capable of causing disease in mammals, including humans.

The term "pathogen-inactivating-effective amount" of an active agent for a pathogen present in a material means sufficient quantity or concentration as to reduce or maintain the level of pathogen in the material. The reduction is preferably to a non-pathogenic level.

The term "biological fluid" refers to mixtures containing one or more bioorganic compounds, e.g. red blood cells, proteins, carbohydrates, nucleic acids, amino acids, lipids, hormones, etc, and/or one or more clinically significant constituents and/or pharmacologically active components. Bioorganic compounds may be of clinical significance and/or have pharmacological activity. A biological fluid might be a solution, liquid mixture, suspension, or a paste. The term further includes whole fluids (such as blood), as well as fractions, extracts, dialyzates, effluents, and other products of chemical, chromatographic, etc. separations. Thus, the term includes blood, blood fractions, blood extracts, blood plasma, protoplasm, milk, urine, semen, saliva, plant extracts, reaction products derived from vaccine production, cell culture supernatants, and other fluids, of either natural or synthetic origin (e.g., recombinant or transgenic); and various isolates, effluents, and extracts taken therefrom.

The term "materials of clinical significance" or "clinically significant constituents" refers to desired components, for instance bioorganic compounds and/or salts that are physiologically active and/or physiologically acceptable, or materials having clinical or therapeutic activity, either as an agonist or antagonist, that may be present in biological fluids or derived of biological origin, whether natural, transgenic, or recombinant. The term includes biologically significant species such as RBCs, hormones, proteins, polysaccharides, lipids, amino acids, and nucleic acids.

The term "disinfect" means to remove, kill, destroy, or render non-pathogenic an otherwise pathogenic component. Likewise, the term "pathogen inactivation" or "pathogen inactivating" means killing, destroying, or rendering non-pathogenic an otherwise pathogenic component of a pathogenic species. To render non-pathogenic means to impair a vital function of the pathogen or merely reduce it in number or concentration such that a host's immune system can dispose of it. Examples of pathogenic components are virus, bacterium, fungus, parasites and other pathogenic microorganisms.

The term "biological system" means multi-cellular organisms and includes mammals, particularly human.

Unless stated otherwise, all quantities or concentrations expressed as a percentage (%) are percent by weight.

Discussion of Experimental Results

TO phototreatment using 80 µM dye and 7.4 J/cm$^2$ of cool white light inactivated 5.1-7.4 log$_{10}$ of tested enveloped viruses, including one ds DNA virus, one ds RNA virus, and negative and positive sense ss RNA viruses. In addition, >6.3 log$_{10}$ of intracellular HIV was photoinactivated. Although non-enveloped viruses were not tested, it is likely that their sensitivity to photoinactivation will be dependent on the permeability of their viral capsids to nucleic acid binding photosensitizing dyes because viruses with tightly interdigitating virus capsid proteins limit dye access to target nucleic acids (Wagner S J et al. Transfusion 34:521-526, 1994; Hanson C V, Blood Cells 1992; 18:7-25).

TO phototreatment of RBC suspensions containing bacteria resulted in great differences in measured levels of inactivation, depending on the bacterial species. Interestingly, the proclivity of an organism to TO photoinactivation cannot be predicted by gram positive or gram negative staining, ruling out simple explanations of cell wall permeability as a determining factor. Surprisingly, the degree of inactivation of a resistant bacteria could be enhanced by as much as 2 log$_{10}$ by decreasing the incubation time from 60 to 15 minutes prior to illumination.

RBC storage properties were evaluated after TO phototreatment under virucidal conditions that did not employ quenchers or competitive inhibitors. When compared to another flexible nucleic acid staining dye, TP, that, unlike TO, strongly binds to RBC membranes in the absence of competitive inhibitor, TO phototreated red cells exhibited less cell damage (Wagner S J et al. Transfusion 2005; 45:752-60). For example, the initial rate of potassium leakage from TO treated RBCs was only 22% of the initial rate of TP treated RBCs (FIG. 4, Wagner S J et al. Transfusion 2005; 45:752-60). In addition, ATP levels of TO phototreated erythrocytes were comparable to controls throughout storage, while day 42 ATP levels of TP phototreated RBCs declined from those of controls by ≈40% (FIG. 5, Wagner S J et al. Transfusion 2005; 45:752-60). Although hemolysis levels during storage of TO and TP phototreated RBCs suspended in RAS-2 were similar (FIG. 3, Wagner S J et al. Transfusion, 2005; 45:752-60), this additive solution protects against colloidal osmotic hemolysis of ion permeable RBCs (Wagner S et al. Transfusion 2002; 42:1200-1205; Pooler J P. Biochim Biophys Acta 1985; 812: 199-205; Besselink G A et al. Vox Sang 2003; 85:183-9). If phototreated RBCs are instead suspended in an additive solution, like ADSOL, which is not protective against colloidal osmotic hemolysis, day 42 hemolysis of TO and TP phototreated RBCs are dissimilar (1.6±0.6%, n=3, TO [data not shown], versus 24.6±7.6%, n=3, TP (Wagner S et al. Transfusion 2005; 45:752-60) p=0.03). These results, along with the protective effect of competitive membrane binding inhibitors of previous studies (Wagner, S J et al., Photochem Photobiol 2002; 76:514-517; Wagner, S J, et al. Transfusion, 2005; 45:752-60), suggest that the photodynamic action of RBC-bound photosensitizers may produce ion leakage that leads to colloidal osmotic hemolysis in non-protective additive solutions. Thus, photochemicals like TO, with high nucleic acid affinity and low RBC affinity, are desirable for pathogen reduction in RBCs because the amount damage generated by RBC-bound dye is minimized.

Leukodepleted 20% hematocrit RBCs suspended in Erythrosol (RAS-2) were oxygenated, inoculated with test organisms, incubated with TO, and illuminated with 7.4 J/cm$^2$ of cool white light. Control and treated samples were analyzed by appropriate assay. Identically prepared, but uncontaminated samples were phototreated, concentrated to 45% hematocrit, and assayed for potassium leakage, hemolysis and ATP during storage.

Approximately 21% TO bound to RBCs. Phototreatment inactivated 7.1 log$_{10}$ of VSV, 6.2 log$_{10}$ of BVDV, 5.4 log$_{10}$ of PRV, 6.7 log$_{10}$ of bacteriophage ø6, >6.5 log$_{10}$ of extracellular HIV, >6.3 log$_{10}$ of intracellular HIV, >7.0 log$_{10}$ of S. epidermidis, 2.4 log$_{10}$ of S. aureus, >6.8 log$_{10}$ of D. radiodurans, 6.4 log$_{10}$ of Y. enterocolitica, 2.3 log$_{10}$ of P. fluorescens, 2.8 log$_{10}$ of S. liquefaciens, 3.5 log$_{10}$ of S. marcescens, and 5.3 log$_{10}$ of E. coli.

Phototreated RBCs exhibited slightly increased hemolysis after 42 days of storage compared to controls (0.43±0.2 versus 0.13±0.05, p<0.05), and moderately elevated potassium efflux compared to controls (7.7±1.1 vs. 4.1±0.7 mM on day 1). ATP levels of treated samples were similar to controls throughout 42 day storage.

EXPERIMENTAL

Photosensitizer

Thiazole Orange or 1-methyl-4-[(3-methyl-2(3H)-benzothiazolylidene)methyl]quinoliniump-tosylate (lot # 08629LI, 90% purity) was purchased from Sigma-Aldrich (Milwaukee, Wis.). Aqueous stocks of 1 mM in RAS-2 were prepared on the same day of an experiment. The structure of TO is given in FIG. 1.

RBC Preparation

Whole blood (500±50 ml) was collected in 70 mL CDP in triple-pack container systems (PL146 primary container, Baxter Healthcare, Deerfield, Ill.) by the Research Blood Department, Holland Laboratory. The packed red cells were separated from platelet-rich plasma by centrifugation at 2620×g for 4 minutes. After platelet-rich plasma and buffy coat were removed, erythrocytes were resuspended in RAS-2 additive solution to approximately 50-60% hematocrit and subsequently leukoreduced. (Leukotrap-SC RC, Pall Medical, East Hills, N.Y.). RBC suspensions in a 600 mL container (PL146 plastic, Baxter Healthcare) were oxygenated by adding 230 mL of a 60:40 percent $O_2:N_2$ gas mixture to 150 mL of RBC suspension, and by subsequent incubation for 30 minutes at 1 to 6° C. with agitation (orbital shaker, 100 r.p.m., 19-mm orbit, VWR Scientific, West Chester, Pa.). Oxygen partial pressures were measured using a blood gas analyzer (Rapid lab 348, Bayer Corp., Medfield Mass.) and were routinely supersaturated with levels greater than 400 mm Hg.

Source of Viruses, Cells and Bacteria

VSV was provided by Meg Lieu (Hyland Diagnostics, Duarte, Calif.). Vero cells (CCL-81) were purchased from American Type Culture Collection (ATCC, Manassas, Va.). Bovine viral diarrhea virus (BVDV, VR-1422) and MBDK (CCL-22) were obtained from the ATCC. Pseudorabies virus (PRV) was provided by Shirley Mieka (American Red Cross, Rockville, Md.). HIV-1 IIIB, and an actively replicating, HIV-1 infected HUT 78 permissive B-cell line, BP-1 (originally isolated by Bernard Poiesz using the method of Federico and colleagues [34]), were obtained from M. Khalid Ijaz (MicroBioTest, Sterling, Va.). Bacteriophage (φ6 and its host *Pseudomonas syringae pv. phaseolicola*, strain HB10Y, were obtained from Christina Burch (University of North Carolina, Chapel Hill, N.C.). Clinical strains of *Escherichia coli* and *Pseudomas fluorescens* were provided by Joseph Campos (Childrens' National Medical Center, Washington, D.C.). Clinical strain of *Serratia marcescens* and *Yersinia enterocolitica* (serotype O:3) was provided by Vince Piscitelli (Yale New Haven Hospital, New Haven, Conn.). *Staphylococcus epidermidis* (ATCC #1228), *Staphylococcus aureus* (ATCC #27217), and *Serratia liquifaciens* (ATCC #27529) and *Deinococcus radiodurans* (ATCC #13939) were purchased from the ATCC (Manassas, Va.).

Phototreatment

Viruses or bacteria were added into approximately 50-60% hematocrit RBCs with subsequent addition of additive solution and TO to obtain 20% final hematocrit containing 80 μM of the dye. The final volume of the pathogen spike was equal to 10% for mammalian viruses and equal to 1% for bacteriophage and bacteria. RBC suspensions containing dye were incubated for 60 minutes and 2 ml aliquots were transferred to polystyrene culture dishes (50 mm bottom diameter) to produce a 1 mm blood film. For some bacterial experiments, RBC suspensions were incubated for different times prior to illumination. All samples except controls were placed on air-cooled transparent stage and illuminated with cool white light (F20T12-CW fluorescent bulbs, General Electric, Circleville, Ohio). A fluence rate of 8.2 mW/cm$^2$ was measured by an optical power meter (model 371, United Detector Technology, Hawthorn, Calif.) equipped with a silicone diode detector and radiometric filter (400-1000 nm, model 115-9, United Detector Technology). All phototreated samples were exposed for 15 minutes to the light source, corresponding to a 7.4 J/cm$^2$ light exposure. Horizontal reciprocal shaking of 70 cycles per minute was applied during phototreatment.

For RBC storage studies, samples were prepared in an identical fashion as inactivation studies, except the pathogen spike was replaced with the same volume of additive solution. Identically phototreated samples were pooled together into PL142 transfer packs and concentrated to 45% hematocrit by centrifugation.

Dye Binding Assay

A spectroscopic assay was developed to measure TO binding to RBCs suspended in RAS-2. Freshly prepared RBCs were mixed with TO and additional RAS-2 to obtain 20% Hct and 80 μM dye concentration. The mixture was incubated for 60 minutes at room temperature, the sample was centrifuged at 6800×g for 4 minutes, and supernatant was analyzed using UV/VIS spectrometer Lambda 40 (Perkin-Elmer, Norwalk, Conn.). A positive control was prepared by adding 80 μM TO directly to the supernatant of 20% Hct RBCs suspended in RAS-2. All spectra were read against a blank containing the supernatant of 20% Hct RBCs.

Mammalian Virus Assay

VSV and PRV plaque assays were carried out using Vero plating cells. BVDV plaque formation was analyzed on MDBK cells. Plaque assays were performed as previously described (Wagner S J et al. *Transfusion* 38:729-737, 1998; Wagner S et al. *Transfusion* 2002; 42:1200-1205; Wagner S J et al. *Photochem Photobiol* 2002; 76:514-517; Wagner S J et al. *Transfusion* In press). Briefly, cells were seeded onto 6-well tissue culture plates and were grown to confluency in RPMI-1640 supplemented with 10% fetal bovine serum (FBS). Control and treated samples were serially diluted 10-fold, plated onto indicator cells and incubated for 30-45 minutes, depending on the virus strain, at 37° C. in 5% CO2 atmosphere with constant gentle rocking. A semi-liquid agar layer (0.15%) was added to each well and infected monolayers were incubated 1 day for VSV, 4 days for PRV or 7 days for BVDV. After incubation, the agar layer was removed and monolayers were stained with 0.1% crystal violet solution in 90% ethanol for at least 15 minutes. The stain was washed by water and plaques were enumerated.

Titration of extracellular and actively replicating intracellular HIV-1 was carried out by MicroBioTest, Sterling, Va. Control and phototreated RBCs containing extracellular or intracellular HIV-1 were serially diluted 10-fold in RPMI-1640 supplemented with glutamine (ATCC, Manassas, Va.) and containing 10% fetal bovine serum (Invitrogen, Calif.), and 0.5 mL of each dilution of control or phototreated sample was transferred into 24-well plates (Corning, Acton, Mass.) in quadruplicate. To each of these wells was added 1 mL of a T-cell lymphoblastic host cell line, CCRF-CEM, for coculture (Yamada O et al. *AIDS Res Hum Retroviruses* 1988; 4:287-94). Virus and host cells were incubated at 37° C. in 5% $CO_2$ in air for 18-24 hours for virus adsorption, and then one-half of the cell suspension was replaced with fresh medium. Infected cells were incubated an additional 3-4 weeks with a replacement of one-half of the volume of the supernatant with fresh medium 3 times per week. After 9-12 additions of fresh media, the culture fluid was assayed by HIV-1 p24 antigen enzyme-linked immunosorbent assay (Zepto Matrix, Buffalo, N.Y.).

Bacteriophage Assay

We prepared stock suspension of bacteriophage ø 6 by plating 104 of plaque purified phage with 0.4% top agar and 200 µl of *P. phaseolicola* suspension grown overnight from a single colony. After 24 hours, the top agar was collected and phage was extracted with equal volume of LB broth. For bacteriophage ø 6 plaque assays, control and treated samples were serially diluted 100-fold and plated onto LB agar plates with 0.8% molten top agar and 200 µl of *P. phaseolicola* suspension grown overnight from a single colony. Plates were incubated overnight at room temperature and plaques were enumerated.

Viral Assays

All virus assays were individually tested for cytotoxicity and interference. No cytotoxicities or interferences were noted at dilutions used for any virus assay. The virus titers of stock cultures and initial titers in red cells appear in table 1. $\log_{10}$ reduction values were calculated by subtracting the $\log_{10}$ titer/mL of RBCs with viable virus after illumination, or the $\log_{10}$ limit of detection/mL of RBCs without viable virus after illumination, from the measured $\log_{10}$ titer/mL of unilluminated RBCs.

Bacterial Assay

We prepared bacterial stocks by inoculating a single colony into 5 mL of Luria broth (LB) and incubating cultures overnight under aerobic conditions at 30 or 37° C., depending on the strain. Control and treated samples were serially diluted 100-fold in unbuffered saline and 0.1 or 1.0 ml were plated onto LB agar plates using 0.8% molten top agar. Colonies were counted after 24-72 hours of incubation at 30 or 37° C., with time and incubation temperature depending on the strain. Colonies were counted from all plates that contained between 1 and 750 colonies per plate.

All bacterial assays were individually tested for cytotoxicity and interference. No cytotoxicities or interferences were noted at the dilutions used for assay, with the exception of *S. aureus*, whose initial counts were reduced approximately 100-fold in blood from expected values. Table 1 gives the initial CFU/mL of stock cultures, and the measured $\log_{10}$ CFU/mL in blood. Log reduction values were calculated from CFU/mL measured in blood and, if no colonies were observed, by the limit of detection in a manner analogous to those described for viruses. Therefore, determination of *S. aureus* reduction by TO and light did not include this 2 $\log_{10}$ reduction in bacterial counts from contact with blood.

RBC Assays

We assayed for ATP using the method of Beutler (A manual of biochemical methods. Third Edition, by Earnest Beutler. Grune & Stratton Inc., Orlando, Fla 1984). Supernatant Hb was determined by the tetramethylbenzidine method (Procedure No. 527, Sigma) (Standefer J C et al. *Clin Chem* 1977; 23:749-51). Total hemoglobin was determined by an automated cell counter (Cell Dyn 3700, Abbott Laboratories, Abbott Park, Ill.). We measured extracellular potassium using blood gas analyzers (RapidLab 348 or RapidLab 860, Bayer Corp, City, State).

Statistics

Determination of means and standard deviation of experimental values, the performance of two-tailed, t tests with Welch's correction, and linear regressions were carried out by using standard software (Instat, GraphPad Software, San Diego, Calif.). A value of p<0.05 was considered significant.

If no organisms were detected in a sample of volume (v) from a larger volume (V) that was phototreated, the Poisson distribution was used to calculate the number of organisms that would be expected to be present with 95% probability according to the following formula:

$$p = [(V-v)/V]n$$

where p is the probability of no viruses or bacteria being detected, or 0.05, and n is the number of organisms distributed in V. See, FDA, Guidance for Industry, Q5A viral safety evaluation of biotechnology products derived from cell lines of human or animal origin, September. 1998, appendix 3 (http//www.fda.gov/cder/guidance/Q5A-fnl.pdf). The limit of detection was defined as n/V and the values of $\log_{10}$ (n/V) appear in Table 1.

TABLE 1

| | $\log_{10}$ (titer/mL or CFU/mL) | | |
|---|---|---|---|
| Organism | Stock | RBC | Limit of Detection |
| VSV | 9.4 | 8.2 | 0.7 |
| PRV | 7.6 | 6.4 | 0.7 |
| BVDV | 7.1 | 6.5 | 0.7 |
| Extracellular HIV | 8.8 | 7.3 | 0.8 |
| Intracellular HIV | 8.2 | 7.1 | 0.8 |
| Bacteriophage φ6 | 10.0 | 7.5 | 0.3 |
| *S. epidermidis* | 9.0 | 8.0 | 0.3 |
| *S. aureus* | 9.6 | 6.6 | 0.3 |
| *Y. enterocolitica* | 9.8 | 8.7 | 0.3 |
| *E. coli* | 9.4 | 8.6 | 0.3 |
| *P. fluorescens* | 9.2 | 8.3 | 0.3 |
| *S. liquefaciens* | 9.9 | 8.7 | 1.4 |
| *S. marcescens* | 9.8 | 8.9 | 0.3 |
| *D. radiodurans* | 8.9 | 7.3 | 0.3 |

Results

Figure 2:
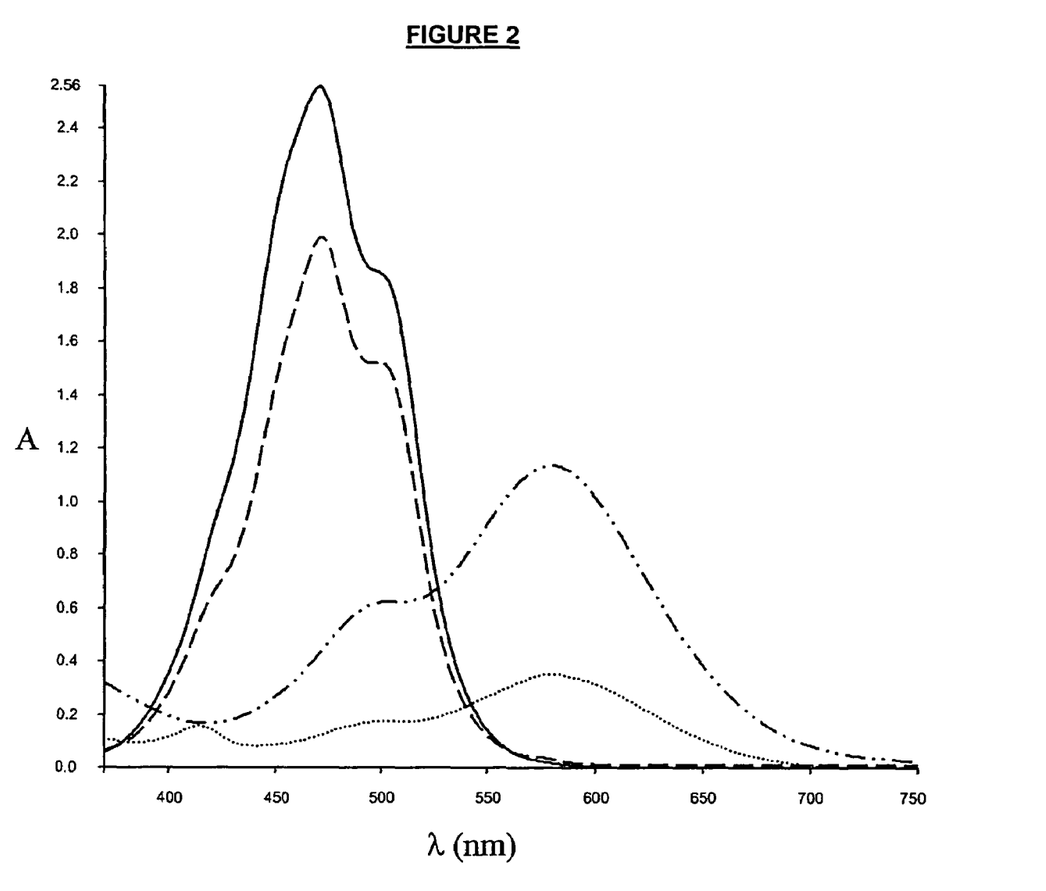
FIG. 2. TO spectra. Solid line: spectra of TO added directly to red cell supernatant; Dashed line: spectra of supernatant containing TO after addition to RBCs and centrifugation. In separate experiments, TP spectra are superimposed on TO spectra for comparison purposes Dotted and dashed line: spectra of TP added directly to red cell supernatant; Dotted line: spectra of supernatant containing TP after addition to RBCs and centrifugation. Spectra shown are representative of those obtained from multiple experiments (TO: n=4; TP: n=5).

RBC Binding Studies. FIG. 2 shows typical TO spectra in the supernatant of the RBCs compared with a positive control. The adsorption peak has a maximum at approximately 470 nm. TO incubation with RBCs for 60 minutes decreases the adsorption peak by 20.5±6.4% (dashed line) (n=4). The supernatant absorption peak (590 nm) of another flexible photosensitizer, TP, is also shown in FIG. 2 for comparative purposes. In contrast to results with TO, the absorption peak of TP decreases by 65.9±6.1% (n=5) when TP is incubating with RBCs, indicating significantly more binding of TP for RBCs than TO for RBCs (p<0.05).

Virus Inactivation Studies. Results from TO virus photoinactivation studies are given in Table 2. Treatment with 80 µm TO and 7.4 J/cm² cool white light could inactivate a double stranded (ds) DNA, several single stranded (ss) RNA, and one ds RNA viruses: 7.1±0.2 $\log_{10}$ inactivation of VSV, 6.2±0.1 $\log_{10}$ inactivation of BVDV, 5.4±0.7 $\log_{10}$ of PRV inactivation, 6.7±0.7 $\log_{10}$ bacteriophage φ6 inactivation, >6.5 $\log_{10}$ of extracellular HIV, and >6.3 $\log_{10}$ of intracellular HIV.

TABLE 2

| Virus | Nucleic Acid Type | Inactivation $\log_{10}$ |
|---|---|---|
| VSV | (−) ss RNA | 7.1 ± 0.2 (n = 4) |
| PRV | ds DNA | 5.4 ± 0.7 (n = 4) |
| BVDV | (+) ss RNA | 6.2 ± 0.1 (n = 3) |
| Extra-HIV | dimeric (+) ss RNA | >6.5 (n = 3) |
| Intra-HIV | RNA, DNA, Provirus | >6.3 (n = 3) |
| φ6 | ds RNA | 6.7 ± 0.7 (n = 3) |

Bacteria Inactivation Studies. Bacteria inactivation studies were carried out at identical conditions as virus inactivation studies. Results are shown in Table 3. TO phototreatment resulted in significant differences in bacteria decontamination: four species were inactivated 5-7 $\log_{10}$ while another four species were inactivated 2-3 $\log_{10}$. In other experiments where the incubation times prior to illumination was varied, the level of inactivation of more resistant species such as *S. aureus* could be increased by 2 $\log_{10}$ by decreasing the incubation time prior to illumination from 60 to 15 minutes.

TABLE 3

| Organism | Inactivation Log$_{10}$ | Gram Staining |
|---|---|---|
| Staphylococcus epidermidis | >7.0 (n = 4) | Gram Positive |
| Staphylococcus aureus | 2.4 ± 0.7 (n = 4) | Gram Positive |
| Deinococcus radiodurans | >6.8 (n = 3) | Gram Positive |
| Yersinia enterocolitica | 6.4 ± 2.0 (n = 4) | Gram Negative |
| Pseudomonas fluorescens | 2.3 ± 1.2 (n = 4) | Gram Negative |
| Serratia liquefaciens | 2.8 ± 0.6 (n = 4) | Gram Negative |
| Serratia marcescens | 3.5 ± 2.5 (n = 3) | Gram Negative |
| Escherichia coli | 5.3 ± 2.0 (n = 4) | Gram Negative |

RBC Storage Studies.

Figure 3:
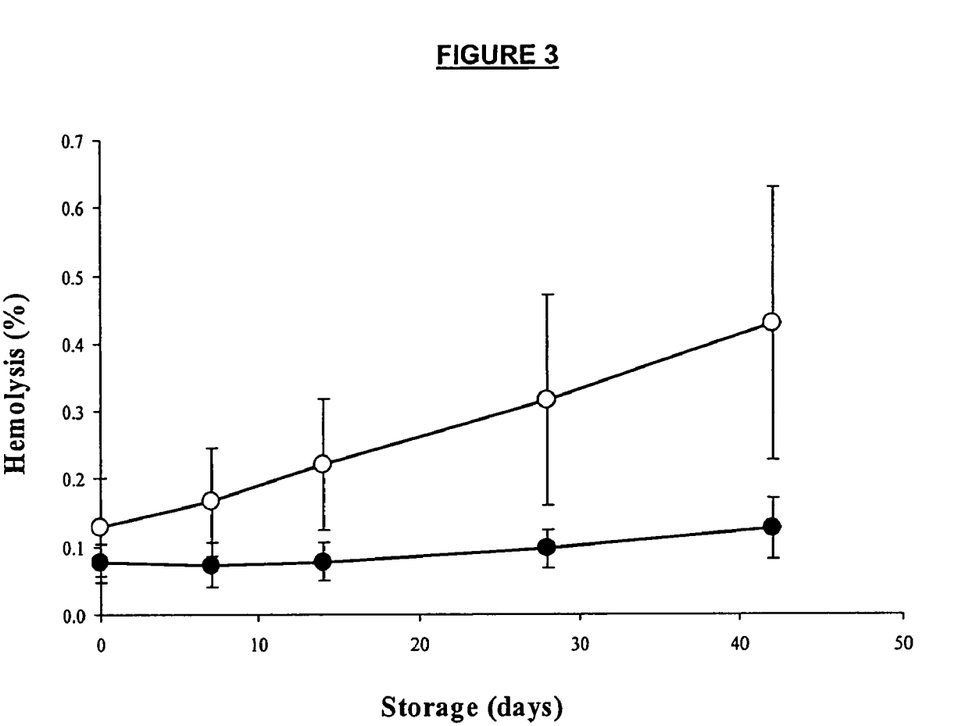
FIG. 3. Hemolysis during storage. Closed circles: controls; open circles: 80 µM TO+7.4 J/cm$^2$ light.

Hemolysis of control and phototreated RBCs during 42 days of refrigerated storage is shown in FIG. 3. RBCs treated with 80 μM TO and 7.4 J/cm$^2$ light have acceptable, but increased levels of hemolysis compared to controls following 42 day storage (0.43±0.2 versus 0.13±0.05, p=0.0054, n=8). In a control experiment, RBCs treated with TO and maintained in the dark yielded similar levels of hemolysis (0.31% on day 42, data not shown) as TO phototreated samples, suggesting that most of the observed hemolysis is caused by the dye alone and is not associated with photodynamic action.

Figure 4:
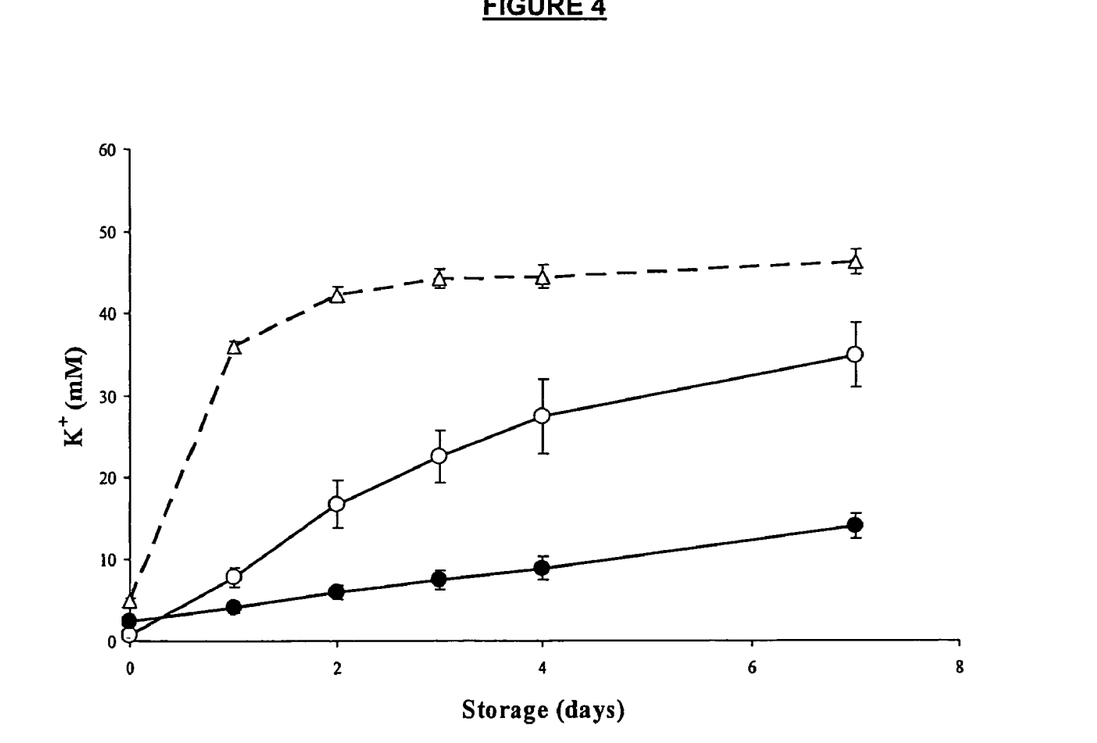
FIG. 4. Potassium leakage during storage. Closed circles: controls; open circles: 80 µM TO+7.4 J/cm$^2$ light; open triangles: 160 µM TP+1.1 J/cm$^2$ light.

FIG. 4 shows effect of TO phototreatment on potassium efflux from RBCs. Supernatant potassium levels measured on day 1 from phototreated cells are elevated compared with untreated controls (7.7±0.7 mM versus 4.1±0.7 mM, p<0.0001, n=8).

Figure 5:
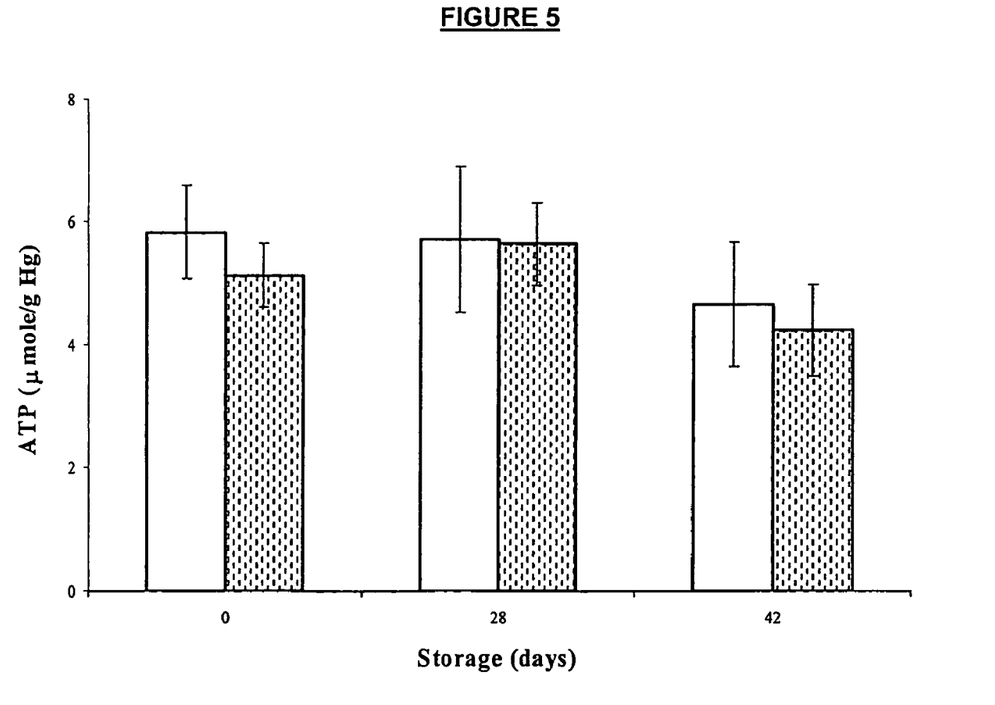
FIG. 5. ATP levels during storage. Open columns: controls; dashed columns: 80 µM TO+7.4 J/cm$^2$ light.

The impact of TO phototreatment on ATP levels of RBCs suspended in RAS-2 is shown in FIG. 5. No significant differences were observed in ATP levels between phototreated and control samples during 42 day storage. At the end of storage, phototreated and control samples had ATP levels of 4.7±1.1 and 4.2±0.8 μmole/g Hg, respectively (p=0.2407, n=8). This represents 80 and 83%, respectively, of initial levels measured on day 0.

What is claimed is:

1. A method for disinfecting a biological fluid containing red blood cells comprising:
   (a) creating a mixture of the biological fluid and a nucleic acid binding, cell-membrane-permeable, asymmetric cyanine dye;
   (b) irradiating the resulting mixture to achieve a viral inactivation capacity corresponding to at least about 7 Log$_{10}$ VSV; and
   (c) assaying the biological fluid for a pathogen;
   wherein the asymmetric cyanine dye has the structure of Formula I:

Formula I where: $R^1$, $R^2$, and $R^3$ are saturated or unsaturated hydrocarbons of $C_6$ or fewer; $R^4$ and $R^5$ are the same or different and are selected from saturated or unsaturated hydrocarbons, acyl, aryl, alcohol, ester, aldehyde, ketone and amine of $C_4$ or fewer, any of which may be further substituted with a halogen, or $R^4$ and/or $R^5$ is itself a halogen; n is 0-5; m is 0-4; p is 0-4; and the ring W is a fused, bicyclic heteroaryl moiety.

2. The method of claim 1, wherein $R^1$ and $R^3$ are saturated or unsaturated hydrocarbons of $C_3$ or fewer, n, m, and p are 0, and W is a fused bicyclic heteroaryl moiety.

3. The method of claim 1, wherein the asymmetric cyanine dye is thiazole orange.

4. The method of claim 1, further comprising the step of assaying the irradiated mixture for a virus.

5. The method of claim 1, wherein the asymmetric cyanine dye in the mixture is at least about 50 μM.

6. The method of claim 1, further comprising the step of incubating the mixture prior to irradiation for about 5 to about 60 minutes.

7. The method of claim 1, wherein the cyanine dye-containing biological fluid is irradiated with about 5 to about 10 J/cm$^2$ white light.

8. The method of claim 1, wherein the method effects no more than about 1.0% hemolysis on storage at 42 days following irradiation.

9. The method of claim 1, wherein potassium efflux from the red blood cells is less than 30 mM on storage at four days following irradiation.

10. A method for disinfecting a biological fluid containing red blood cells comprising:
    (a) creating a mixture of the biological fluid containing red blood cells and a nucleic acid binding, cell-membrane-permeable asymmetric cyanine dye;
    (b) irradiating the resulting mixture to achieve a viral inactivation capacity corresponding to at least about 7 Log 10VSV and less than 2% hemolysis on storage at 42 days following irradiation; and
    (c) recovering intact red blood cells from the mixture;
    wherein the asymmetric cyanine dye has the structure of Formula I:

Formula I where: $R^1$, $R^2$ and $R^3$ are saturated or unsaturated hydrocarbons of $C_6$ or fewer; $R^4$ and $R^5$ are the same or different and are selected from saturated or unsaturated hydrocarbons, acyl, alcohol, ester, aldehyde and amine of $C_4$ or fewer, any of which may be further substituted with a halogen, or $R^4$ and/or $R^5$ is itself a halogen; n is 0-5; m is 0-4; p is 0-4; and the ring W is a fused, bicyclic heteroaryl moiety.

11. The method of claim 10, wherein the mixture is irradiated with at least about 5 to about 10 J/cm$^2$ white light.

12. The method of claim 10, wherein the method effects no more than about 1.0% hemolysis on storage at 42 days following irradiation.

13. The method of claim 10, wherein potassium efflux from the red blood cells is less than 30 mM on storage at four days following irradiation.

14. The method of claim 10, wherein the asymmetric cyanine dye in the mixture is at least about 50 µM.

15. The method of claim 10, further comprising the step of assaying the irradiated mixture for a virus.

16. The method of claim 10, wherein the asymmetric cyanine dye is added to the mixture at about 80 µM; the mixture is incubated prior to irradiation for about 5 to about 60 minutes; the mixture is irradiated with at least about 5 J/cm² white light; and the resulting mixture is assayed for a pathogen.

17. The method of claim 10, wherein the cyanine dye has the structure of Formula I:

Formula I where: $R^1$, $R^2$, and $R^3$ are saturated or unsaturated hydrocarbons of $C_6$ or fewer; $R^4$ and $R^5$ are the same or different and are selected from saturated or unsaturated hydrocarbons, acyl, aryl, alcohol, ester, aldehyde, ketone and amine of $C_4$ or fewer, any of which may be further substituted with a halogen, or $R^4$ and/or $R^5$ is itself a halogen; n is 0-5; m is 0-4; p is 0-4; and the ring W is a fused, bicyclic heteroaryl moiety; and
wherein the asymmetric cyanine dye produces singlet oxygen upon irradiation when binding with a nucleic acid molecule.

18. The method of claim 10, wherein the asymmetric cyanine dye produces singlet oxygen upon irradiation when binding with a nucleic acid molecule.

19. The method of claim 17, wherein the method effects no more than about 1.0% hemolysis on storage at 42 days following irradiation.

20. The method of claim 17, wherein n, m and p are 0; $R_1$ and $R_3$ are both —$CH_3$, and W is quinoline.

21. A method for disinfecting a biological fluid containing red blood cells comprising:

(a) creating a mixture of the biological fluid and a nucleic acid binding, cell-membrane-permeable, asymmetric cyanine dye;
(b) irradiating the resulting mixture with white light to achieve:
  (i) viral inactivation corresponding to at least about 7 $Log_{10}$ VSV; and
  (ii) less than 2% hemolysis on storage at 42 days following irradiation; and
(c) assaying the biological fluid for a pathogen;
wherein the asymmetric cyanine dye has the structure of Formula I:

Formula I where: $R^1$, $R^2$, and $R^3$ are saturated or unsaturated hydrocarbons of $C_6$ or fewer; $R^4$ and $R^5$ are the same or different and are selected from saturated or unsaturated hydrocarbons, acyl, aryl, alcohol, ester, aldehyde, ketone and amine of $C_4$ or fewer, any of which may be further substituted with a halogen, or $R^4$ and/or $R^5$ is itself a halogen; n is 0-5; m is 0-4; p is 0-4; and the ring W is a fused, bicyclic heteroaryl moiety; and
wherein the asymmetric cyanine dye produces singlet oxygen upon irradiation with white light only when intercalated with a nucleic acid molecule.

22. The method of claim 21, wherein $R^1$ and $R^3$ are saturated or unsaturated hydrocarbons of $C_3$ or fewer; n, m, and p are 0, and W is a fused bicyclic heteroaryl moiety.

23. The method of claim 21, wherein in the compound of Formula I, n, m and p are 0; $R_1$ and $R_3$ are —$CH_3$, and W is quinoline.

24. The method of claim 21, wherein the method effects no more than about 1.0% hemolysis on storage at 42 days following irradiation.

* * * * *